United States Patent [19]

Lundberg

[11] 4,096,147
[45] Jun. 20, 1978

[54] SUBSTITUTED AZASTEROIDS

[75] Inventor: Charles Andrew Lundberg, Cincinnati, Ohio

[73] Assignee: Richardson-Merrell Inc., Wilton, Conn.

[21] Appl. No.: 574,101

[22] Filed: May 2, 1975

Related U.S. Application Data

[63] Continuation-in-part of Ser. No. 350,390, Apr. 12, 1973, abandoned.

[51] Int. Cl.² .......................................... C07D 455/06
[52] U.S. Cl. ......................... 260/287 AZ; 260/283 R; 260/283 SY; 260/287 D; 260/289 D; 260/289 AZ; 260/465 R; 260/570.8 R; 260/650 R; 560/103; 568/715; 568/814
[58] Field of Search ................. 260/287 AZ, 289 AZ

[56] References Cited

U.S. PATENT DOCUMENTS

| | | | |
|---|---|---|---|
| 3,219,668 | 11/1965 | Brown et al. | 260/287 AZ |
| 3,346,582 | 10/1967 | Brown et al. | 260/289 AZ |
| 3,378,560 | 4/1968 | Brown et al. | 260/289 AZ |

OTHER PUBLICATIONS

Tietz, "Clinical Chemistry," 1971, pp. 496–497.
White et al., "Principles of Biochemistry," 1968, pp. 522–524.
Burger, Medicinal Chemistry, 1963, p. 42.
Morrison et al., Organic Chemistry, (1966), pp. 790–791.
Strandtmann et al., "J. of Org. Chem.," 31, p. 797, (1966).
Meyers et al., "Tetrahedron Letters," (1965), No. 4, pp. 255–260.

*Primary Examiner*—Donald G. Daus
*Assistant Examiner*—David E. Wheeler
*Attorney, Agent, or Firm*—L. Ruth Hattan; Eugene O. Retter; George W. Rauchfuss, Jr.

[57] ABSTRACT

Compounds of the following general formula are useful as antidepressant and antiparkinson agents:

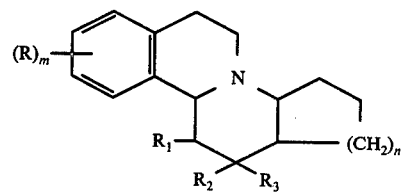

wherein R represents hydrogen, hydroxy, halogen, trifluoromethyl, straight or branched lower alkyl of from 1 to 6 carbon atoms, straight or branched lower alkoxy of from 1 to 6 carbon atoms, acyloxy, alkoxycarbonyloxy, carbamoyloxy, benzoyloxy, or benzoyloxy substituted with straight or branched lower alkyl of from 1 to 6 carbon atoms, straight or branched lower alkoxy of from 1 to 6 carbon atoms or halogen; $R_1$ represents hydrogen, straight or branched lower alkyl of from 1 to 6 carbon atoms, phenyl or benzyl; $R_2$ represents hydrogen, straight or branched lower alkyl of from 1 to 6 carbon atoms, ethynyl, ethynyl substituted with straight or branched lower alkyl of from 1 to 6 carbon atoms; aryl, or aralkyl wherein each aryl moiety may be substituted with straight or branched lower alkyl of from 1 to 6 carbon atoms, straight or branched lower alkoxy of from 1 to 6 carbon atoms or halogen; $R_3$ represents hydroxy, acyloxy, alkoxycarbonyloxy, carbamoyloxy, benzoyloxy or benzoyloxy substituted with straight or branched lower alkyl of from 1 to 6 carbon atoms, straight or branched lower alkoxy of from 1 to 6 carbon atoms or halogen; or $R_2$ and $R_3$ taken together form an oxo group; $m$ is an integer of 1 or 2; and $n$ is an integer of from 1 to 3. Individual optical and geometric isomers and pharmaceutically acceptable acid addition salts of the compounds are also included within the scope of this invention.

17 Claims, No Drawings

SUBSTITUTED AZASTEROIDS

This application is a continuation-in-part of application Ser. No. 350,390 filed Apr. 12, 1973, now abandoned.

Field of Invention

This invention relates to quinolizine derivatives and their use as antidepressant and antiparkinson agents.

Description of Prior Art

The preparation of two compounds which are included within the scope of this invention, that is 2,3,4,4a, 6,7,11b,12,13,13a-decahydro-1H-dibenzo[a,f]-quinolizin-13-one and 1,2,3,3a,5,6,10b,11,12,12a-decahydrobenzo[a]cyclopenta[f]quinolizin-12-one is described by A. I. Meyers et al. in Tetrahedron Letters 1965, 255–60. To applicant's knowledge no pharmacological utility for these or any other compounds of this invention has been reported previously.

SUMMARY OF THE INVENTION

Compounds of the following general Formula I are useful as antidepressant and antiparkinson agents:

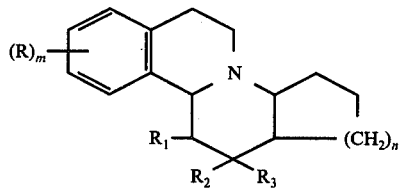

Formula I wherein R is selected from hydrogen, hydroxy, halogen, trifluoromethyl, straight or branched lower alkyl of from 1 to 6 carbon atoms, straight or branched lower alkoxy of from 1 to 6 carbon atoms,

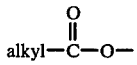

wherein the alkyl moiety contains from 1 to 6 carbon atoms and can be straight or branched, alkoxycarbonyloxy, carbamoyloxy, benzoyloxy and benzoyloxy substituted with straight or branched lower alkyl of from 1 to 6 carbon atoms, straight or branched lower alkoxy of from 1 to 6 carbon atoms or halogen; $R_1$ is selected from hydrogen, straight or branched lower alkyl of from 1 to 6 carbon atoms, phenyl and benzyl; $R_2$ is selected from hydrogen, straight or branched lower alkyl of from 1 to 6 carbon atoms, ethynyl, ethynyl substituted with straight or branched lower alkyl of from 1 to 6 carbon atoms, phenyl, benzyl, 2-phenethyl, substituted phenyl, substituted benzyl and substituted 2-phenethyl wherein the substituents are on any position of the aromatic ring of each of phenyl, benzyl and 2-phenethyl and each is selected from straight or branched lower alkyl of from 1 to 6 carbon atoms, straight or branched lower alkoxy of from 1 to 6 carbon atoms and halogen; $R_3$ is selected from hydroxy,

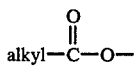

wherein the alkyl moiety has from 1 to 6 carbon atoms and may be straight or branched, alkoxycarbonyloxy, carbamoyloxy, benzoyloxy or benzoyloxy substituted with straight or branched lower alkyl of from 1 to 6 carbon atoms, straight or branched lower alkoxy of from 1 to 6 carbon atoms or halogen; or $R_2$ and $R_3$ taken together form an oxo group; $m$ is an integer of 1 or 2; and $n$ is an integer of from 1 to 3. Individual optical and geometric isomers and pharmaceutically acceptable acid addition salts of the compounds are also included within the scope of this invention.

DETAILED DESCRIPTION OF INVENTION

Illustrative examples of lower alkyl groups containing from 1 to 6 carbon atoms, as used herein, are methyl, ethyl, n-propyl, isopropyl, n-butyl, tert-butyl, pentyl and hexyl.

Illustrative examples of lower alkoxy groups containing from 1 to 6 carbon atoms, as used herein, are methoxy, ethoxy, n-propoxy, isopropoxy, tert-butoxy, pentyloxy and hexyloxy.

The term alkoxycarbonyloxy, as used herein, is taken to mean the group

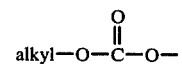

wherein the alkyl moiety contains from 1 to 6 carbon atoms and may be straight or branched.

The term carbamoyloxy, as used herein, is taken to mean the group

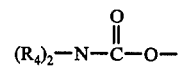

wherein $R_4$ is hydrogen, a straight or branched lower alkyl group of from 1 to 6 carbon atoms, or aryl.

As examples of substituted benzoyloxy groups there may be mentioned 3,4,5-trimethoxybenzoyloxy, p-toluoyloxy, p-chlorobenzoyloxy and p-tert-butylbenzoyloxy. Illustrative examples of substituted phenyl, benzyl and 2-phenethyl groups are anisyl, p-tolyl, m-ethylphenyl, p-chlorophenyl, p-ethoxybenzyl, 3,4,5-trimethoxybenzyl and p-methylphenethyl.

As examples of substituted ethynyl groups there may be mentioned 1-propynyl, 1-butynyl, 1-pentynyl, and 1-isopentynyl.

As examples of compounds of general Formula I there may be mentioned the following:

2,3,4,4a,6,7,11b,12,13,13a-decahydro-12-methyl-1H-dibenzo[a,f]quinolizin-13-one, 2,3,4,4a,6,7,11b,12,13,13a-decahydro-9-10-dimethoxy-12-methyl-1H-dibenzo[a,f]quinolizin-13-one, 2,3,4,4a,6,7,11b,12,13,13a-decahydro-1H-dibenzo[a,f]-quinolizin-13-one, 1,2,3,3a,5,6,10b,11,12,12a-decahydro-9-hydroxy-12-phenylbenzo[a]cyclopenta[f]quinolizin-12-one, 1,2,3,3a,5,6,10b,11,12,12a-decahydro-8,9-diethoxybenzo[a]-cyclopenta[f]quinolizin-12-one, 1,2,3,4,5,5a,7,8,12b,13,14,14a-dodecahydro-10,12-dichlorobenzo[a]cyclohepta[f]quinolizin-14-one, 1,2,3,4,5,5a,7,8,12b,13,14,14a-dodecahydro-11-hexyl-benzo[a]cyclohepta[f]quinolizin-14-one, 1,2,3,3a, 5,6,10b,11,12,12a-decahydrobenzo[a]cyclopenta-[f]quinolizin-12-one, 2,3,4,4a,6,7,11b,12,13,13a-decahydro-9,10-dimethoxy-1H-dibenzo[a,f]quinolizin-13-one, 2,3,4,4a,6,7,11b,12,13,13a-decahydro-10-chloro-1H-dibenzo[a,f]quinolizin-13-one,
2,3,4,4a,6,7,11b,12,13,13a-decahydro-1H-dibenzo[a,f]quinolizin-13-ol,
2,3,4,4a,6,7,11b,12,13,13a-decahydro-9,10-dimethoxy-1H-dibenzo[a,f]quinolizin-13-ol,
2,3,4,4a,6,7,11b,12,13,13a-decahydro-12-methyl-1H-dibenzo[a,f]quinolizin-13-ol,
2,3,4,4a,6,7,11b,12,13,13a-decahydro-9,10-dimethoxy-12-methyl-1H-dibenzo[a,f]quinolizin-13-ol,
1,2,3,3a,5,6,10b,11,12,12a-decahydrobenzo[a]cyclopenta-[f]quinolizin-12-ol,
12-ethynyl-1,2,3,3a,5,6,10b,11,12,12a-decahydrobenzo-[a]cyclopenta[f]quinolizin-12-ol,
2,3,4,4a6,7,11b,12,13,13a-decahydro-1H-dibenzo[a,f]quinolizin-13-ol propionate ester,
2,3,4,4a,6,7,11b,12,13,13a-decahydro-1H-dibenzo[a,f]quinolizin-13-ol carbamate ester,
1,2,3,4,5,5a,7,8,12b,13,14,14a-dodecahydro-10,12-dichlorobenzo[a]cyclohepta[f]quinolizin-14-ol,
1,2,3,4,5,5a,7,8,12b,13,14,14a-dodecahydro-10,12-dichlorobenzo[a]cyclohepta[f]quinolizin-14-ol benzoate ester,
1,2,3,3a,5,6,10b,11,12,12a-decahydro-9-hydroxy-12-phenylbenzo[a]cyclopenta[f]quinolizin-12-one butyrate ester,
2,3,4,4a,6,7,11b,12,13,13a-decahydro-10-hydroxy-1H-dibenzo[a,f]quinolizin-13-ol dicarbomethoxy ester,
1,2,3,4,5,5a,7,8,12b,13,14,14a-dodecahydro-14-(1-butynyl)benzo[a]cyclohepta[f]quinolizin-14-ol,
1,2,3,3a,5,6,10b,11,12,12a-decahydro[a]cyclopenta[f]quinolizin-12-ol carbethoxy ester, and
2,3,4,4a,6,7,11b,12,13,13a-decahydro-13-(p-tolyl)-1H-dibenzo[a,f]quinolizin-13-ol.

A preferred embodiment of this invention is compounds of general Formula I wherein m is the integer 1.

Another preferred embodiment of this invention is compounds of general Formula I wherein n is the integer 1 or 2.

Another preferred embodiment of this invention is compounds of general Formula I wherein the R substituents are attached to the 6- and 7-positions of the isoquinoline moiety as represented by the following general Formula I (a):

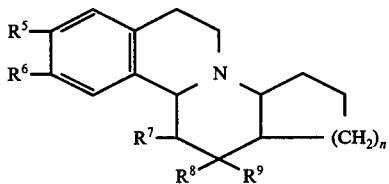

Formula I (a)

wherein each of $R^5$ and $R^6$ is selected from hydrogen, chlorine, fluorine, bromine, iodine, hydroxy, straight or branched lower alkoxy of from 1 to 4 carbon atoms, straight or branched lower alkyl of from 1 to 4 carbon atoms, trifluoromethyl,

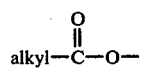

wherein the alkyl moiety has from 1 to 4 carbon atoms and may be straight or branched, alkoxycarbonyloxy, carbamoyloxy, benzoyloxy, and benzoyloxy substituted with straight or branched lower alkyl of from 1 to 4 carbon atoms, straight or branched lower alkoxy of from 1 to 4 carbon atoms, chlorine fluorine, bromine, and iodine with the proviso that when one of $R^5$ and $R^6$ is trifluoromethyl, the other of $R^5$ and $R^6$ is other than trifluoromethyl; $R^7$ is selected from hydrogen, straight or branched lower alkyl of from 1 to 4 carbon atoms, phenyl and benzyl $R^8$ is selected from hydrogen, straight or branched lower alkyl of from 1 to 4 carbon atoms, phenyl, benzyl, 2-phenethyl, substituted phenyl, substituted benzyl, substituted 2-phenethyl wherein the substituents are on any position of the aromatic ring of each of phenyl, benzyl, and 2-phenethyl and each substituent is selected from straight or branched lower alkyl of from 1 to 4 carbon atoms, straight or branched lower alkoxy of from 1 to 4 carbon carbon atoms, chlorine, fluorine, bromine, and iodine; $R^9$ is selected from hydroxy, the group

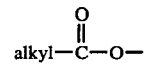

wherein the alkyl moiety has from 1 to 4 carbon atoms and may be straight or branched, alkoxycarbonyloxy, carbamoyloxy, benzoyloxy, and benzoyloxy substituted with straight or branched lower alkyl of from 1 to 4 carbon atoms, straight or branched lower alkoxy of from 1 to 4 carbon atoms, chlorine, fluorine, bromine and iodine; and n has the meaning defined in general Formula I, that is, is an integer of from 1 to 3. Preferably, n is 1 or 2.

Another preferred embodiment of this invention is compounds of general Formula I (a) wherein $R^7$ is selected from hydrogen; a straight chain alkyl of from 1 to 4 carbon atoms selected from methyl, ethyl, n-propyl and n-butyl; phenyl and benzyl.

Another preferred embodiment of this invention is compounds of general Formula I (a) wherein the alkyl moieties in the various $R^5$, $R^6$, $R^7$, $R^8$ and $R^9$ substituents is a straight chain alkyl of from 1 to 4 carbon atoms.

Another preferred embodiment of this invention is compounds of general Formula I (a) wherein $R^5$ is hydrogen, and $R^6$ is selected from hydrogen, chlorine, fluorine, bromine, iodine, hydroxy, straight or branched lower alkoxy of from 1 to 4 carbon atoms, straight or branched lower alkyl of from 1 to 4 carbon atoms, trifluoromethyl,

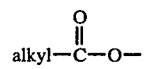

wherein the alkyl moiety has from 1 to 4 carbon atoms and may be straight or branched, alkoxycarbonyloxy, carbamoyloxy, benzoyloxy and benzoyloxy substituted with straight or branched lower alkyl of from 1 to 4 carbon atoms, straight or branched lower alkoxy of from 1 to 4 carbon atoms, chlorine, fluorine, bromine, and iodine.

Another preferred embodiment of this invention is compounds of general Formula I (a) wherein $R^6$ is hydrogen, and $R^5$ is selected from chlorine, fluorine, bromine, iodine, hydroxy, straight or branched lower alkoxy of from 1 to 4 carbon atoms, straight or branched lower alkyl of from 1 to 4 carbon atoms, trifluoromethyl,

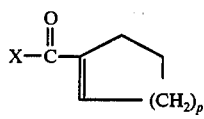

Formula III

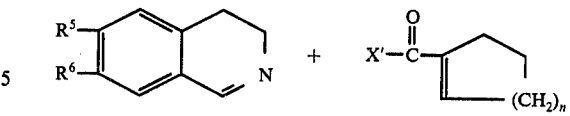

Formula II (a)   Formula III (a)

In the above Formulas II (a) and III (a), $R^5$ and $R^6$ have the meanings defined in general Formula I (a), p is an integer of 1 to 3, and $X'$ is straight or branched lower alkyl of from 1 to 5 carbon atoms, for example, methyl, ethyl, propyl, isopropyl, butyl and tert-butyl, benzyl and phenethyl.

Following the procedure described hereinabove using reactants of Formulas II (a) and III (a) will give the oxo precursors of the compounds of general Formula I (a).

The compounds of this invention wherein $R^2$ is hydrogen and $R^3$ is hydroxy, that is compounds of the following general Formula IV and as represented by general Formula IV (a) for the preferred compounds:

wherein the alkyl moiety has from 1 to 4 carbon atoms and may be straight or branched, alkoxycarbonyloxy, carbamoyloxy, benzoyloxy and benzoyloxy substituted with straight or branched lower alkyl of from 1 to 4 carbon atoms, straight or branched lower alkoxy of from 1 to 4 carbon atoms, chlorine, fluorine, bromine and iodine.

Another preferred embodiment of this invention is compounds of general Formula I (a) wherein each of $R^5$ and $R^6$ is selected from hydrogen, chlorine, fluorine, bromine, iodine, hydroxy, straight or branched lower alkoxy of from 1 to 4 carbon atoms, straight or branched lower alkyl of from 1 to 4 carbon atoms, and trifluoromethyl with the proviso that when one of $R^5$ or $R^6$ is trifluoromethyl, the other of $R^5$ and $R^6$ is other than trifluoromethyl.

The compounds of general Formula I wherein $R_2$ and $R_3$ together form an oxo group are prepared by reacting a 3,4-dihydroisoquinoline derivative of the formula

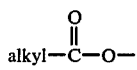

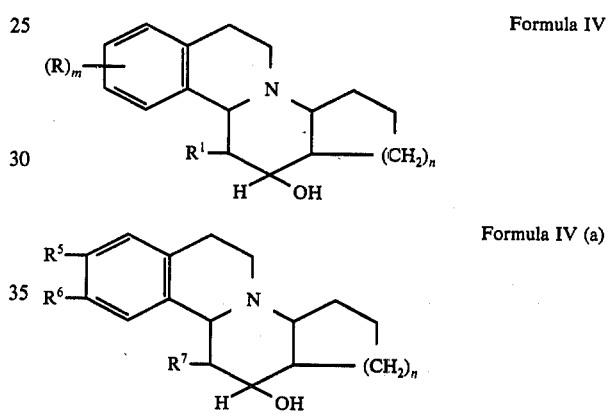

Formula IV

Formula IV (a)

wherein R and m have the meanings defined hereinbefore with a ketone derivative of the formula

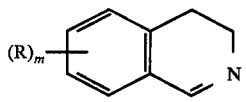

Formula II wherein X represents straight or branched lower alkyl of from 1 to 7 carbon atoms, for example, methyl, ethyl, n-propyl, butyl, heptyl and the like, benzyl or phenethyl, and p is an integer of from 1 to 3. This reaction may be carried out with or without a solvent. Suitable solvents for this reaction are lower alcohols, such as, methanol, ethanol, isopropyl alcohol, n-butanol and the like; dimethylformamide, dimethylsulfoxide; aromatic solvents, such as, for example, benzene, toluene, xylene, and the like; and halogenated hydrocarbon solvents such as for example, chloroform. This reaction may be carried out in the presence of an acid catalyst such as hydrochloric acid or p-toluenesulfonic acid, preferably one equivalent of the acid catalyst. The reaction time may vary from about 30 minutes to about 60 hours depending upon the reactants, the solvent employed, if any, and the reaction temperature which may vary from about 40° C to about 150° C. The product obtained on work-up may be isolated as the free base or the acid addition salt.

The above reaction scheme to give the oxo precursors of the compounds of general Formula I (a) may be illustrated as follows:

wherein R, $R^1$, $R^5$, $R^6$, $R^7$, m and n have the meanings defined hereinabove are prepared by reducing the corresponding ketone derivatives, that is, compounds of general Formula I wherein $R^2$ and $R^3$ together form an oxo group. This reduction reaction may be carried out using reducing agents such as sodium borohydride, lithium aluminum hydride, or lithium tri-(sec-butyl)-borohydride or by catalytic hydrogenation. This reaction is carried out in an appropriate solvent such as lower alcohols, that is, an alcohol having from 1 to 4 carbon atoms, for example, ethanol, ethers or cyclic ethers, such as diethyl ether or tetrahydrofuran. In addition, when the reduction is accomplished by catalytic hydrogenation, solvents such as acetic acid or halogenated hydrocarbon such as methylene chloride may be used. The reaction time varies up to 60 hours depending upon the reducing agent employed. A preferred reaction time is from about 30 minutes to about 2 hours. The temperature of the reaction may vary from about −20° C to about 80° C. Preferably the reaction is carried out at room temperature.

Compounds wherein R and $R^3$ in general Formula I and $R^5$, $R^6$, and $R^9$ in general Formula I (a) represent

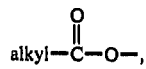

alkoxycarbonyloxy, carbamoyloxy, benzoyloxy or substituted benzoyloxy, or wherein R in general Formula I and R[5] and R[6] in general Formula I (a) represent acyloxy, alkoxycarbonoyloxy, carbamoyloxy, benzoyloxy or substituted benzoyloxy are prepared from the corresponding alcohol, that is, compounds wherein R[3] and/or R in general Formula I and wherein R[9] and/or R[5] and R[6] in general Formula I (a) represent hydroxy by standard esterification of the alcohol with an appropriate alkyl acid wherein the alkyl moiety contains from 1 to 6 carbon atoms and may be straight or branched, or the acid halide or anhydride thereof, or with benzoic acid or benzoic acid substituted with straight or branched lower alkyl of from 1 to 6 carbon atoms, straight or branched lower alkoxy of from 1 to 6 carbon atoms, or halogen, or the acid halide or anhydride thereof, or with alkoxycarbonyl halide wherein the alkoxy moiety contains from 1 to 6 carbon atoms and may be straight or branched. Compounds wherein R and R[3] in general Formula I and R[5] and R[6] and R[9] in general Formula I (a) represent carbamoyloxy are prepared from the corresponding alcohol by reaction with an isocyanate derivative of the formula O=C=N—R[4] or with a carbamoyl halide derivative of the formula $$halo-\overset{O}{\underset{\|}{C}}-N(R_4)_2$$

wherein R[4] has the meaning defined hereinbefore, by standard procedures. The various reactants may be selectively chosen to give the desired derivative as represented by Formulas I and I (a).

Compounds of general Formula I wherein R[2] and general Formula I (a) wherein R[7] is other than hydrogen, ethynyl or substituted ethynyl are prepared from the corresponding ketone derivative, that is, compounds of general Formula I wherein R[2] and R[3] together form an oxo group, by reaction with a Grignard reagent of the formula R[10]MgX by standard procedures wherein R[10] represents a straight or branched lower alkyl group of from 1 to 6 carbon atoms, aryl or aralkyl wherein each aryl moiety may be substituted with a straight or branched lower alkyl group of from 1 to 6 carbon atoms, a straight or branched lower alkoxy group of from 1 to 6 carbon atoms, or halogen. The Grignard reagent described can be selectively chosen to give the desired compounds of Formulas I and I (a).

Compounds of general Formula I wherein R[2] and general Formula I (a) wherein R[9] represent ethynyl or ethynyl substituted with a straight or branched lower alkyl of from 1 to 6 carbon atoms are prepared according to the general procedure described by J. W. Huffman and P. G. Arapakos, J. Org. Chem. 30, 1604 (1965) by the reaction of lithium with an alkyne derivative, for example, acetylene in the presence of an alkylenediamine, for example, ethylenediamine.

The 3,4-dihydroisoquinoline starting materials which find use in this invention may be prepared by reacting an appropriately substituted phenethylamine of the following general Formula V or general Formula V (a) in reference to the preferred compounds of the invention as represented by general Formula I (a)

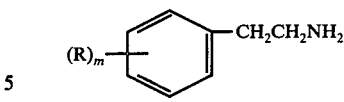

Formula V

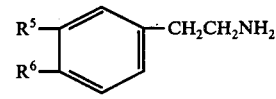

Formula V (a)

wherein R, R[5], R[6] and m have the meanings defined in general Formulas I and I (a) with formic acid or alkylformate followed by dehydration with, for example, polyphosphoric acid or phosphorusoxychloride.

There are a number of general procedures for preparing the appropriately substituted phenethylamines known in the art as for example, the procedure described by E. F. Kiefer, J. Med. Chem. 15, 214 (1972) whereby an appropriately substituted benzyl alcohol is treated with a hydrohalo acid, for example, hydrochloric acid to give the corresponding benzyl halide which is treated with sodium cyanide to give the corresponding nitrile derivative. The nitrile derivative is reduced with a mixture of lithium aluminum hydride and aluminum chloride to give the appropriately substituted phenethylamine. The appropriately substituted benzylhalide intermediate wherein the substituents on the benzyl halide do not contain a benzylic proton may be obtained by halogenation of the corresponding tolyl derivative by the action of N-bromo- or N-chlorosuccinamide by procedures generally known in the art. The appropriately substituted benzyl alcohol derivative may be obtained by reduction of the corresponding carboxylic acid or lower alkyl ester thereof or the corresponding benzaldehyde by, for example, lithium aluminum hydride reduction. The appropriately substituted benzoic acid derivative may be obtained from the corresponding nitro or amine derivative by standard methods, for example, the nitro derivative can be reduced with tin and hydrochloric acid to give the corresponding amine which is diazotized with for example, nitrous acid then reacted with cuprous cyanide and hydrolyzed with aqueous acid to give the corresponding carboxylic acid.

Most of the starting materials used to prepare the appropriately substituted phenethylamines are commercially available, or known in the art, or can be prepared by procedures known in the art, as for example, those described above. The higher alkoxy substituted starting materials can be prepared by alkylation of the corresponding hydroxy derivative using standard procedures, such as, reaction with alkylhalide in the presence of sodium carbonate. The appropriately substituted nitrobenzene derivatives described above in obtaining the carboxylic acid derivatives can be prepared by treating variously known disubstituted benzene compounds with nitric acid in sulfuric acid. The alkoxy substituted nitrobenzene derivatives can also be prepared by treating benzyloxyphenol(CA 73, P 110139s) with an alkyl halide in the presence of a base followed by catalytic hydrogenation with for example, Pd/H[2] and treatment with an appropriate alkyl halide in the presence of a base to give the dialkoxy substituted benzene which can be nitrated by procedures described above. The trifluoromethyl substituted starting materials can be prepared by the reaction of the corresponding benzoic acid derivatives with sulfur tetrafluoride and heating to give the substituted benzene derivatives which can be nitrated as described above, or a substituted nitrobenzoic acid can be treated with sulfur tetrafluoride with heating to give the corresponding trifluoromethyl substituted nitrobenzene derivative.

The following examples are illustrative of the invention.

EXAMPLE 1

2,3,4,4a,6,7,11b,12,13,13a-Decahydro-1H-dibenzo[a,f]-quinolizin-13-ol (A) To a stirred suspension of 32.0 g. (0.125 mole) of 2,3,4,4a,6,7,11b,12,13,13a-decahydro-1H-dibenzo[a,f]-quinolizin-13-one in 275 ml of absolute ethanol is added 4.8 g (0.125 mole) of sodium borohydride in five portions during a period of ten minutes. The mixture is stirred at room temperature for ninety minutes and then diluted with 1200 ml of water and 50 ml of a 50% sodium hydroxide solution. The mixture is extracted twice with ether, and the ether layers are washed with water and saturated sodium chloride solution, dried over magnesium sulfate, filtered and evaporated in vacuo. The residual oily product is dissolved in 1200 ml of boiling hexane, treated with Norite, filtered and concentrated to about 700 ml which is allowed to stand overnight at room temperature. The precipitate is collected and recrystallized from hexane-benzene to give 2,3,4,4a,6,7,11b,12,13a-decahydro-1H-dibenzo[a,f]-quinolizin-13-ol, M.P. 122°–134° C. (mixture of isomers).

(B) A purer sample of the compound is obtained as follows. The residual oily product remaining after removal of the ether is dissolved in 425 ml of boiling hexane, filtered while hot, concentrated to 375 ml and allowed to stand overnight at room temperature. The mother liquor is decanted and the remaining solid is dissolved in a refluxing mixture of 350 ml of hexane and 80 ml of benzene, then allowed to stand overnight at room temperature. The mother liquor is decanted and the remaining solid is dissolved in boiling hexane-benzene then allowed to cool slowly to room temperature. The solution is cooled to 0° C. in an ice-bath. The resulting solid is separated, dried, dissolved in 80 ml of boiling ethanol to which water is added dropwise until the solution becomes turbid. The solution is allowed to cool to room temperature and the precipitate is vacuum dried to give 2,3,4,4a,6,7,11b,12,13,13a-decahydro-1H-dibenzo[a,f]-quinolizin-13-ol, M.P. 140°–142.5° C.

The following products are obtained when in Example 1 (A) appropriate amounts of the ketone derivatives listed below are substituted for 1,2,3,4,4a,6,7,11b,12,13a-decahydrodibenzo[a,f]quinolizin-13-one.

| Example No. | Product | Ketone Derivative |
|---|---|---|
| 2 | 2,3,4,4a,6,7,11b,12,13,13a-decahydro-9,10-dimethoxy-1H-dibenzo-[a,f]quinolizin-13-Ol,M.P. 168–176° C. | 2,3,4,4a,6,7,11b,12,13,13a-decahydro-9,10-dimethoxy-1H-dibenzo[9,f] |
| 3 | 2,3,4,4a,6,7,11b,12,13,13a-decahydro-12-methyl-1H-dibenzo[a,f]-quinolizin-13-ol,M.P. 140–144° C. | 2,3,4,4a,6,7,11b,12,13,13a-decahydro-12-methyl-1H-dibenzo[a,f]quinolizin-13-one |
| 4 | 2,3,4,4a,6,7,11b,12,13,13a-decahydro-9,10-dimethoxy-12-methyl-1H-dibenzo-[a,f]quinolizin-13-ol, M.P. 184–198° C. | 1,2,3,4,4a,6,7,11b,12,13a-decahydro-9,10-dimethoxy-12-methyldibenzo[a,f]-quinolizin-13-one |
| 5 | 2,3,4,4a,6,7,11b,12,13,13a-decahydro-10-methyl-1H-dibenzo[a,f]quinolizin-13-ol, M.P. 134–142° C. | 2,3,4,4a,6,7,11b,12,13,13a-decahydro-10-methyl-1H-dibenzo[a,f]quinolizin-13-one |
| 6 | 1,2,3,3a,5,6,10b,11,12,12a-decahydrobenzo[a]-cyclopenta[f]quinolizin-12-ol, M.P. 119–128° C. | 1,2,3,3a,5,6,10b,11,12,12a-decahydrobenzo[a]cyclopenta[f]quinolizin-12-one |
| 7 | 1,2,3,3a,5,6,10b,11,12,12a-decahydro-9-hydroxy-11-phenylbenzo[a]cyclopenta-[f]quinolizin-12-ol | 1,2,3,3a,5,6,10b,11,12,12a-decahydro-9-hydroxy-11-phenylbenzo[a]cyclopenta[f]quinolizin-12-one |
| 8 | 1,2,3,3a,5,6,10b,11,12,12a-decahydro-8,9-diethoxybenzo[a]cyclopenta[f]-quinolizin-12-ol | 1,2,3,3a,5,6,10b,11,12,12a-decahydro-8,9-diethoxybenzo[a]-cyclopenta[f]quinolizin-12-one |
| 9 | 2,3,4,4a,6,7,11b,13,13a-decahydro-10-butoxy-12-benzyl-1H-dibenzo[a,f]-quinolizin-13-ol | 2,3,4,4a,6,7,11b,12,13,13a-decahydro-10-butoxy-12-benzyl-1H-dibenzo[a,f]quinolizin-13-one |
| 10 | 1,2,3,4,5,5a,7,8,12b,13,14,14a-dodecahydro-11-n-hexylbenzo[a]-cyclohepta[f]quinolizin-12-ol | 1,2,3,4,5,5a,7,8,12b,13,14,14a-dodecahydro-11-n-hexylbenzo[a]cyclohepta[f]quinolizin-12-one |
| 11 | 1,2,3,4,5,5a,7,8,12b,13,14,14a-dodecahydro-10,12-dichlorobenzo[a]-cyclohepta[f]quinolizin-14-ol | 1,2,3,4,5,5a,7,8,12b,13,14,14a-dodecahydro-10,12-dichlorobenzo[a]cyclohepta[f]quinolizin-14-one |

The following products are obtained when in Example 1 (A) appropriate amounts of the ketone derivatives listed below are substituted for 1,2,3,4,4a,6,7,11b,12,13a-decahydrodibenzo[a,f]quinolizin-13-one, the residual oil is additionally treated with excess ethereal hydrochloric acid and the precipitate is recrystallized from butanonemethanol.

| Example No. | Product | Ketone Derivative |
|---|---|---|
| 12 | 10-chloro-2,3,4,4a,6,7,11b,12,13,13a-decahydro-1H-dibenzo[a,f]quinolizin-13-ol hydrochloride, M.P. 238–265° C. | 10-chloro-2,3,4,4a,6,7,11b,12,13,13a-decahydro-1H-dibenzo[a,f]quinolizin-13-one |
| 13 | 10-fluoro-2,3,4,4a,6,7,11b,12,13,13a-decahydro-1H-dibenzo[a,f]-quinolizin-13-ol hydrochloride, M.P. 236–260° C. | 10-fluoro-2,3,4,4a,6,7,11b,12,13,13a-decahydro-1H-dibenzo[a,f]quinolizin-13-one |
| 14 | 1,2,3,3a,5,6,10b,11,12,12a-decahydro-8,9-dimethoxybenzo[a]cyclopenta[f]-quinolizin-12-ol hydrochloride, M.P. 236–247° C. | 1,2,3,3a,5,6,10b,11,12,12a-decahydro-8,9-dimethoxybenzo[a]cyclopentata[f]quinolizin-12-one |

EXAMPLE 15

2,3,4,4a,6,7,11b,12,13,13a-Decahydro-13-methyl-1H-dibenzo[a,f]quinolizin-13-ol To the Grignard reagent prepared from 21.5 g (0.15 mole) of methyl iodide and 3.7 g of magnesium turnings in 120 ml of dry ether is added dropwise 12.5 g (0.05 mole) of 2,3,4,4a,6,7,11b,12,13,13a-decahydro-1H-dibenzo[a,f]-quinolizin-13-one in 125 ml of tetrahydrofuran.

When the addition is complete the mixture is stirred and refluxed overnight, then cooled in an ice-water bath and decomposed by the addition of 15 ml of water and 20 ml of 10% sodium hydroxide solution until the precipitated inorganic salts form a thick paste. The organic layer is decanted and the salts are washed with methylene chloride. The combined organic layers are dried over sodium sulfate filtered and evaporated. The residual oily product is chromatographed on an alumina column using ethyl acetate as the eluent resulting in a yellow oil which solidified on standing. The solid is recrystallized from hexane to give 2,3,4,4a,6,7,11b,12,13,13a-decahydro-13-methyl-1H-dibenzo[a,f]quinolizin-13-ol, M.P. 85°–88° C.

EXAMPLE 16

2,3,4,4a,6,7,11b,12,13,13a-Decahydro-9,10-dimethoxy-13-phenyl-1H-dibenzo[a,f]quinolizin-13-ol hydrochloride To 6.3 g (0.02 mole) of 2,3,4,4a,6,7,11b,12,13,13a-decahydro-9,10-dimethoxy-1H-dibenzo[a,f]quinolizin-13-one in 100 ml of tetrahydrofuran is added dropwise 30 ml of a 2N solution of phenylmagnesium bromide in tetrahydrofuran. When the addition is complete, the mixture is refluxed for three hours and cooled after which 100 ml of saturated ammonium chloride solution is added. The organic and aqueous layers are separated and the aqueous layer is extracted with ether. The combined organic layers are dried over magnesium sulfate, filtered and evaporated in vacuo leaving an oily residue which is dissolved in dry ether and treated with excess ethereal hydrochloric acid. The resulting precipitate is collected and recrystallized from benzene-methanol to give 2,3,4,4a,6,7,11b,12,13,13a-decahydro-9,10-dimethoxy-13-phenyl-1H-dibenzo[a,f]quinolizin-13-ol hydrochloride, M.P. 227°–228° C.

EXAMPLE 17

12-Ethynyl-1,2,3,3a,5,6,10b,11,12,12a-decahydrobenzo[a]cyclopenta[f]quinolizin-12-ol hydrochloride According to the general procedure of J. W. Huffman and P. G. Arapakos, J. Org. Chem. 30, 1604 (1965) 10.0 g (0.042 mole) of 1,2,3,3a,5,6,10b,11,12,12a-decahydrobenzo[a]cyclopenta[f]quinolizin-12-one in 50 ml of tetrahydrofuran is reacted with an excess of lithium acetylide-ethylenediamine. The resulting material is dissolved in ether and treated with excess ethereal hydrochloric acid, and the precipitate is recrystallized from butanone-methanol to give 12-ethynyl-1,2,3,3a,5,6,10b, 11,12,12a-decahydrobenzo[a]cyclopenta[f]quinolizin-12-ol hydrochloride, M.P. 230°–240° C.

EXAMPLE 18

2,3,4,4a,6,7,11b,12,13,13a-Decahydro-1H-dibenzo[a,f]-quinolizin-13-ol propionate ester hydrochloride A solution of 2.2 g (0.0087 mole) of 2,3,4,4a,6,7,11b,12,13,13a-decahydro-1H-dibenzo[a,f]-quinolizin-13-ol and 25 ml of ethyl acetate is treated with 1.8 g (0.02 mole) of propionyl chloride and refluxed overnight. The powdery white solid which separates from the cooled solution is collected, washed with ethyl acetate then ether and is recrystallized from butanone-methanol to give 2,3,4,4a,6,7,11b,12,13,13a-decahydro-1H-dibenzo[a,f]quinolizin-13-ol propionate ester hydrochloride, M.P. 208°–227° C.

When in Example 18 an appropriate amount of the quinolizinol derivatives listed below is substituted for 2,3,4,4a,6,7,11b,12,13,13a-decahydro-1H-dibenzo[a,f]-quinolizin-13-ol, and an appropriate amount of the halide derivatives listed below is substituted for propionyl chloride the respective products also listed below are obtained.

| Example No. | Product | Quinolizinol Derivative | Halide Derivative |
| --- | --- | --- | --- |
| 18A | 2,3,4,4a,6,7,11b,12,13,13a-decahydro-9,10-dimethoxy-13-phenyl-1H-dibenzo[a,f]quinolizin-13-ol benzoate ester hydrochloride | 2,3,4,4a,6,7,11b,12,13,13a-decahydro-9,10-dimethoxy-13-phenyl-1H-dibenzo[a,f]quinolizin-13-ol | benzoyl chloride |
| 19 | 1,2,3,3a,5,6,10b,11,12,12a-decahydro-9-hydroxy-11-phenylbenzo[a]cyclopenta[f]quinolizin-12-ol ethyl carbonate diester hydrochloride | 1,2,3,3a,5,6,10b,11,12,12a-decahydro-9-hydroxy-11-phenylbenzo[a]cyclopenta[f]quinolizin-12-ol | ethyl chloroformate |
| 20 | 1,2,3,4,5,5a,7,8,12b,13,14,14a-dodecahydro-10,12-dichlorobenzo[a]cyclohepta[f]quinolizin-14-ol-N,N-diethylcarbamate hydrochloride | 1,2,3,4,5,5a,7,8,12b,13,14,14a-dedecahydro-10,12-dichlorobenzo[a]cyclohepta[f]quinolizin-14-ol | N,N-diethyl carbamoyl chloride |
| 21 | 2,3,4,4a,6,7,11b,12,13,13a-decahydro-10-methyl-1H-dibenzo[a,f]quinolizin-13-ol propionate, hydrochloride, M.P. 238–251° C. | 2,3,4,4a,6,7,11b,12,13,13a-decahydro-10-methyl-1H-dibenzo[a,f]quinolizin-13-ol | propionyl chloride |

EXAMPLE 22

When in Example 18 appropriate amounts of isobutyryl chloride, acetyl chloride, ethylchloroformate, 3,4,5-trimethoxybenzoyl chloride, ethyl isocyanate and phenyl isocyanate are substituted for propionyl chloride the following respective products are obtained.

2,3,4,4a,6,7,11b,12,13,13a-decahydro-1H-dibenzo[a,f]-quinolizin-13-ol isobutyrate hydrochloride, M.P. 195°–215° C, 2,3,4,4a,6,7,11b,12,13,13a-decahydro-1-H-dibenzo[a,f]-quinolizin-13-ol acetate hydrochloride, 2,3,4,4a,6,7,11b,12,13,13a-decahydro-1H-dibenzo[a,f]-quinolizin-13-ol ethyl carbonate ester hydrochloride, 2,3,4,4a,6,7,11b,12,13,13a-decahydro-1H-dibenzo[a,f]-quinolizin-13-ol 3,4,5-trimethoxybenzoate ester hydrochloride, 2,3,4,4a,6,7,11b,12,13,13a-decahydro-1H-dibenzo[a,f]-quinolizin-13-ol N-ethyl carbamate, and 2,3,4,4a,6,7,11b,12,13,13a-decahydro-1H-dibenzo[a,f]-quinolizin-13-ol N-phenyl carbamate.

EXAMPLE 23

2,3,4,4a,6,7,11b,12,13,13a-Decahydro-12-methyl-1H-dibenzo[a,f]quinolizin-13-one

A mixture of 16.75 g (0.1 mole) of 3,4-dihydroisoquinoline hydrochloride and 28.0 g (0.2 mole) of 1-cyclohexen-1-yl ethyl ketone in 28 ml of ethanol is refluxed for 52 hours then poured into 300 ml of water and extracted with ether. The aqueous layer is separated and made basic by slowly adding ammonium hydroxide solution with stirring. Stirring is continued until a solid is formed after which the liquid is decanted. The solid is washed with water, dissolved in methylene chloride, dried over sodium sulfate and concentrated to an oil. The oil is dissolved in refluxing hexane, filtered and concentrated to a solid which is recrystallized from hexane-benzene to give 2,3,4,4a,6,7,11b,12,13,13a-decahydro-12-methyl-1H-dibenzo[a,f]-quinolizin-13-one, M.P. 144.5°–147.5° C.

When in Example 23 appropriate amounts of the isoquinoline derivatives and the ketone derivatives listed below are employed, the respective products listed below are obtained.

ether. The aqueous layer is made basic with concentrated ammonium hydroxide solution with stirring. Upon the formation of an oil, ice is added to the mixture after which a solid is formed. The solid material is washed with water, dried overnight in a vacuum oven, and recrystallized from hexane to give 1,2,3,3a,5,6,10b,11,12,12a-decahydrobenzo[a]cyclopenta[f]quinolizin-12-one, M.P. 101°–102.5° C.

EXAMPLE 33

2,3,4,4a,6,7,11b,12,13,13a-Decahydro-9,10-dimethoxy-1H-dibenzo[a,f]quinolizin-13-one When in Example 32 appropriate amounts of 3,4-dihydro-6,7-dimethoxyisoquinoline hydrochloride and 1-chylohexen-1-yl methyl ketone respectively are substituted for 3,4-dihydroisoquinoline hydrochloride and 1-cyclopenten-1-yl methyl ketone, 2,3,4,4a,6,7,11b,12,13,13a-decahydro-9,10-dimethoxy-1H-dibenzo[a,f]quinolizin-13-one is obtained M.P. 129°–141° C.

EXAMPLE 34

2,3,4,4a,6,7,11b,12,13,13a-Decahydro-10-fluoro-1H-dibenzo[a,f]quinolizin-13-one

A mixture of 19.5 g (0.1 mole) of 3,4-dihydro-7-fluoroisoquinoline hydrochloride and 18.6 g (0.15 mole) of 1-cyclohexen-1-yl methyl ketone in 22 ml of ethanol is reluxed with stirring overnight then cooled to room temperature. The solution is poured into water, whereupon a suspension of undissolved material forms, and is extracted with ether. The aqueous layer and its suspended solid is stirred and treated with ammonium

| Example No. | Product | Isoquinoline Hydrochloride Derivative | Ketone Derivative |
|---|---|---|---|
| 24 | 1,2,3,3a,5,6,10,11,12,12a-decahydro-9-hydroxy-11-phenylbenzo[a]cyclopenta-[f]quinolizin-12-one | 3,4-dihydro-7-hydroxyisoquinoline | 1-cyclopenten-1-yl benzyl ketone |
| 25 | 1,2,3,3a,5,6,10b,11,12,12a-decahydro-8,9-diethoxybenzo-[a]cyclopenta[f]quinolizin-12-one | 6,7-diethoxy-3,4-dihydro-isoquinoline | 1-cyclopenten-1-yl methyl ketone |
| 26 | 2,3,4,4a,6,7,11b,12,13,13a-decahydro-10-butoxy-12-benzyl-1H-dibenzo[a,f]quinolizin-13-one | 7-butoxy-3,4-dihydroiso-quinoline | 1-cyclohexen-1-yl phenethyl ketone |
| 27 | 1,2,3,4,5,5a,7,8,12b,13,14,14a-dodecahydro-11-n-hexyl-benzo[a]cyclohepta[f]quinolizin-14-one | 3,4-dihydro-7-n-hexyliso-quinoline | 1-cyclohepten-1-yl methyl ketone |
| 28 | 1,2,3,4,5,5a,7,8,12b,13,14,14a-dodecahydro-10,12-dichlorobenzo[a]cyclohepta[f]quinolizin-14-one | 6,8-dichloro-3,4-dihydroiso-quinoline | 1-cyclohepten-1-yl methyl ketone |
| 29 | 2,3,4,4a,6,7,11b,12,13,13a-decahydro-9,10-dimethoxy-12-methyl-1H-dibenzo[a,f]quinolizin-13-one | 3,4-dihydro-6,7-dimethoxy-isoquinoline | 1-cyclohexen-1-yl ethyl ketone |
| 30 | 2,3,4,4a,6,7,11b,12,13,13a-decahydro-1H-dibenzo[a,f]-quinolizin-13-one, M.P. 112–140° C. | 3,4-dihydroisoquinoline | 1-cyclohexen-1-yl methyl ketone |
| 31 | 2,3,4,4a,6,7,11b,12,13,13a-decahydro-10-methyl-1H-dibenzo[a,f]quinolizin-13-one | 3,4-dihydro-7-methyl-isoquinoline | 1-cyclohexen-1-yl methyl ketone |

EXAMPLE 32

1,2,3,3a,5,6,10b,11,12,12a-Decahydrobenzo[a]cyclopenta[f]quinolizin-12-one

A mixture of 16.7 g (0.1 mole) of 3,4-dihydroisoquinoline hydrochloride and 27.0 g (0.02 mole) of 1-cyclopenten-1-yl methyl ketone in 22 ml of ethanol is refluxed overnight then evaporated to dryness. The remaining solid is dissolved in water and washed with hydroxide solution to pH 8.5 to 9.0. The suspended solid is broken up, collected by decantation, washed with water, dissolved in methylene chloride, dried over sodium sulfate and evaporated. The residue is dissolved in benzene and chromatographed on alumina and eluted with benzene. The resulting solid is triturated with hexane and dried to give 2,3,4,4a,6,7,11b,12,13,13a- decahydro-10-fluoro-1H-dibenzo[a,f]quinolizin-13-one, M.P. 130°–136° C.

EXAMPLE 35

2,3,4,4a,6,7,11b,12,13,13a-Decahydro-10-chloro-1H-dibenzo[a,f]quinolizin-13-one

When in Example 34 an appropriate amount of 7-chloro-3,4-dihydroisoquinoline hydrochloride is substituted for 3,4-dihydro-7-fluoroisoquinoline hydrochloride, 2,3,4,4a,6,7,11b,12,13,13a-decahydro-10-chloro-1H-dibenzo[a,f]-quinolizin-13-one is obtained.

EXAMPLE 36

1,2,3,3a,5,6,10b,11,12,12a-Decahydro-8,9-dimethoxybenzo[a]cyclopenta[f]quinolizin-12-one A mixture of 23.0 g (0.1 mole) of 6,7-dimethoxy-3,4-dihydroisoquinoline hydrochloride, 23.0 g (0.2 mole) of 1-cyclopenten-1-yl methyl ketone in 25 ml of ethanol is refluxed overnight then evaporated in vacuo. The residual oil is partitioned between water and ether after which the aqueous layer is separated and washed with ether, made basic with concentrated ammonium hydroxide solution and stirred. A sticky solid material forms which is washed with water, partially dried in vacuo, dissolved in methylene chloride, dried over sodium sulfate, filtered and evaporated. The residual material is dissolved in benzene and chromatographed on alumina eluting with benzene then with benzene-15% ethyl acetate. The solid obtained is recrystallized from benzene-hexane to give 1,2,3,3a,5,6,10b,11,12,12a-decahydro-8,9-dimethoxybenzo[a]cyclopenta[f]quinolizin-12-one, M.P. 105°–114° C.

The compounds of this invention selectively remit reserpine induced extrapyramidal motor deficits, or catalepsy, induced in experimental animals rendering them useful as antidepressants, antiparkinson agents, and useful in the treatment of catalepsy and Parkinsonian-like effects resulting from the administration of neuroleptics. Administration of reserpine to mice, rats, cats and dogs results in motor disturbances of extrapyramidal origin which are generally referred to as catalepsy and also results in symptoms which resemble those of Parkinson's disease, that is, akinesia, rigidity and tremors. In cats and dogs the response is not uniform, but rather varies from a moderate tremor and ataxia to collapse resembling sleep depending upon the dosage administered. In addition there is a peripheral effect as evidenced in mice and rats by paralysis of the eye lid, or ptosis, and in cats and dogs by a paralysis of the nictitating membrane.

The ability of the compounds of this invention to selectively remit reserpine-induced catalepsy, or motor deficits, is demonstrated by a reproducible restoration of motor activity without concurrent remission of such peripheral effects of reserpine as ptosis in rats and mice, or paralysis of the nictitating membrane in cats and dogs. For example, mice of the Swiss Webster strain weighing from 18 to 25 g are given intravenously 2 mg/kg of reserpine and sixty minutes later the test compound is given orally. From 15 to 60 minutes after administration of the test compound observations as to the motor ability of the mouse and remission of ptosis are made. In mice the oral $ED_{50}$ for the selective remission of centrally elicited reserpine deficits of 2,3,4,4a,6,7,11b,12,13,13a-decahydro-1H-dibenzo[a,f]-quinolizin-13-ol is 2.5 mg/kg. In the same test system apomorphine which is known to be effective in the treatment of Parkinson's disease [P. Castaigne et al., Res. Commun. Chem. Pathol. Pharmacol. 2, 154 (1971)] has an $ED_{50}$ of 4.6 mg/kg.

The compounds of this invention can be administered to animals, warm-blooded animals and particularly mammals and humans either alone or in the form of pharmaceutical preparations which contain the novel compounds suitable for oral or parenteral administration. Pharmaceutical perparations containing novel compounds of this invention and conventional pharmaceutical carriers can be employed in unit dosage forms such as solids, for example tablets and capsules, or liquid solutions, suspensions or elixirs for oral administration, or liquid solutions, suspensions, emulsions, and the like for parenteral administration. The quantity of compound administered can vary over a wide range to provide from about 0.1 mg/kg (milligram per kilogram) to about 100 mg/kg of body weight of the patient per day to achieve the desired effect. Unit doses of these compounds can contain from about 5 to 500 mg of the compound and may be administered, for example, from 1 to 4 times daily. The following examples are illustrative of pharmaceutical preparations containing as active ingredients compounds of this invention.

An illustrative composition for tablets is as follows:

|     |     | Per Tablet |
| --- | --- | --- |
| (a) | 2,3,4,4a,6,7,11b,12,13,13a-decahydro-1H-dibenzo[a,f]-quinolizin-13-ol | 100.0 mg |
| (b) | wheat starch | 15.0 mg |
| (c) | lactose | 33.5 mg |
| (d) | magnesium stearate | 1.5 mg |

A portion of the wheat starch is used to make a granulated starch paste which together with the remainder of the wheat starch and the lactose is granulated, screened and mixed with the active ingredient (a), and the magnesium stearate. The mixture is compressed into tablets weighting 150 mg each.

An illustrative composition for a parenteral injection is the following wherein the quantitites are on a weight to volume basis.

|     |     | Amount |
| --- | --- | --- |
| (a) | 10-fluoro-2,3,4,4a,6,7,11b,12,13,13a-decahydro-1H-dibenzo[a,f]-quinolizin-13-ol hydrochloride | 100.0 mg |
| (b) | sodium chloride | q.s. |
| (c) | water for injection to make | 20.0 ml |

The composition is prepared by dissolving the active ingredient (a) and sufficient sodium chloride in water for injection to render the solution isotonic. The composition may be dispensed in a single ampule containing 100 mg of active ingredient for multiple dosage or in 20 ampules for single dosage.

An illustrative composition for a hard gelatin capsule is the following:

|     |     | Amount |
| --- | --- | --- |
| (a) | 2,3,4,4a,6,7,11b,12,13,13a-decahydro-1H-dibenzo[a,f]-quinolizin-13-ol | 200.0 mg |
| (b) | talc | 35.0 mg |

The composition is prepared by passing the dry powders of (a) and (b) through a fine mesh screening and mixing them well. The powder is then filled into No. 0 hard gelatin capsules at a net fill of 235 mg per capsule.

EXAMPLE 37

When in Example 23, 25.5 g (0.1 mole) of 6,7-di-tert-butyl-3,4-dihydroisoquinoline hydrochloride is substituted for 3,4-dihydroisoquinoline, 2,3,4,4a,6,7,11b,12,13,13a-decahydro-9,10-di-tert-butyl-12-methyl-1H-dibenzo[a,f]quinolizin-13-one is obtained. By substituting an appropriate amount of the thus obtained ketone for 2,3,4,4a,6,7,11b,12,13,13a-decahydro-1H-dibenzo[a,f]-quinolizin-13-one in the procedure of Example I(A) 2,3,4,4a,6,7,11b,12,13,13a-decahydro-9,10-di-tert-butyl-12-methyl-1H-dibenzo[a,f]quinolizin-13-ol is obtained.

The 6,7-di-tert-butyl-3,4-dihydroisoquinoline hydrochloride starting material is prepared from ortho-di-tert-butylbenzene which is treated with nitric acid in acetic anhydride to give 3,4-di-tert-butylnitrobenzene. The di-substituted nitrobenzene derivative is hydrogenated over palladium to give the corresponding amine which is diazotized using nitrosonium tetrafluoroborate to give the diazonium salt of 3,4-di-tert-butylaniline (Tetrahedron Letters, 1964(1), 61–64). The diazonium salt derivative is converted to the corresponding phenethylamine which is cyclized to the dihydroisoquinoline by the following reaction sequence.

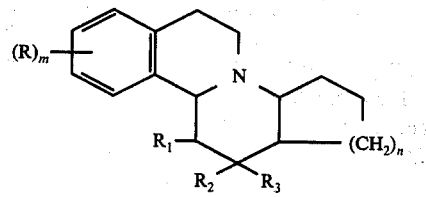

wherein R is selected from hydrogen, hydroxy, halogen, trifluoromethyl, straight or branched lower alkyl of from 1 to 6 carbon atoms, straight or branched lower alkoxy of from 1 to 6 carbon atoms,

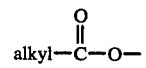

wherein the alkyl moiety has from 1 to 6 carbon atoms and may be straight or branched, alkoxycarbonyloxy, carbamoyloxy, benzoyloxy and benzoyloxy mono-, di- or tri- substituted with straight or branched lower alkyl of from 1 to 6 carbon atoms, straight or branched lower alkoxy of from 1 to 6 carbon atoms or halogen; $R^1$ is selected from hydrogen, straight or branched lower alkyl of from 1 to 6 carbon atoms, phenyl and benzyl; $R^2$ is selected from hydrogen, straight or branched

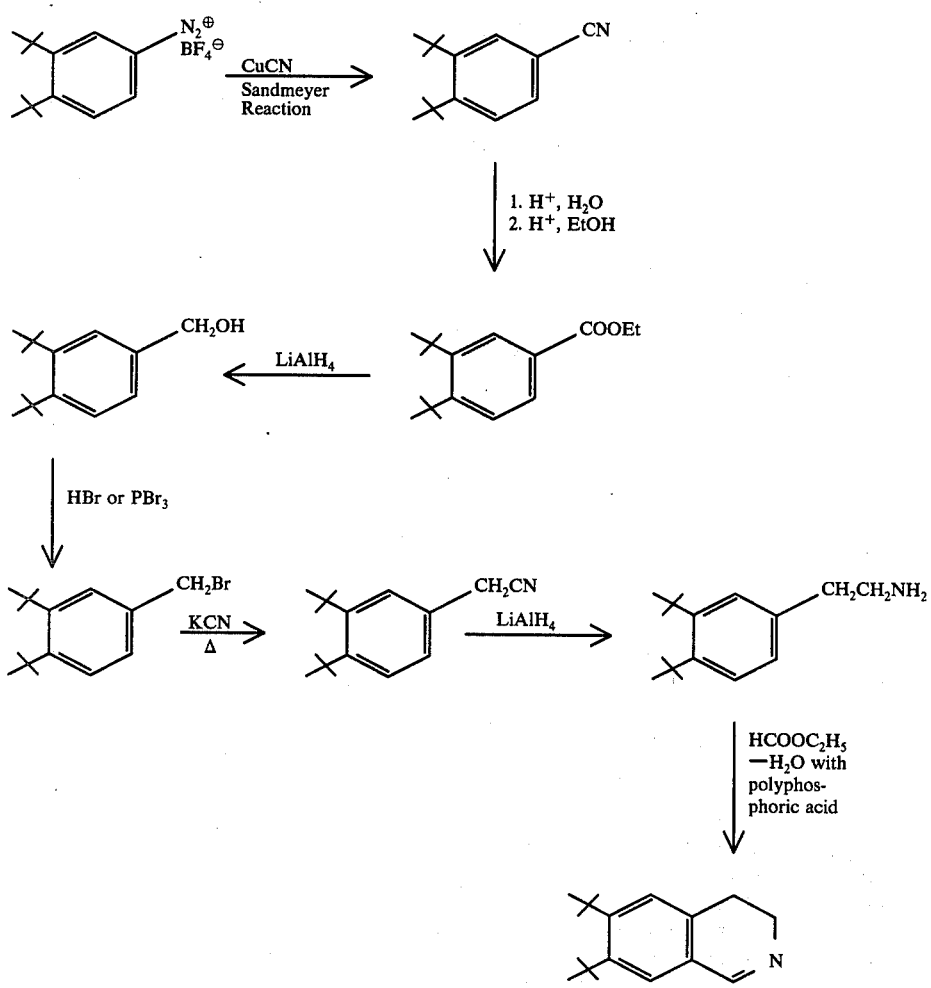

I claim:
1. A compound selected from the formula lower alkyl of from 1 to 6 carbon atoms, ethynyl, ethynyl substituted with straight or branched lower alkyl of from 1 to 6 carbon atoms, phenyl, benzyl, 2-phenethyl, mono-, di- or tri- substituted phenyl, mono-, di- or tri- substituted benzyl and mono-, di- or tri- substituted 2-phenethyl wherein the substituents are on any position of the aromatic ring and are selected from straight or branched lower alkyl of from 1 to 6 carbon atoms, straight or branched lower alkoxy of from 1 to 6 carbon atoms and halogen; $R^3$ is selected from hydroxy,

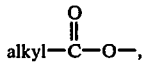

alkoxycarbonyloxy, carbamoyloxy, benzoyloxy and benzoyloxy mono-, di- or tri- substituted with straight or branched lower alkyl of from 1 to 6 carbon atoms, straight or branched lower alkoxy of from 1 to 6 carbon atoms or halogen; m is an integer of 1 or 2; n is an integer of from 1 to 3; and pharmaceutically acceptable acid addition salts thereof.

2. A compound of claim 1 wherein n is the integer 1 or 2.

3. A compound of claim 1 wherein R is selected from hydrogen, hydroxy, halogen, trifluoromethyl, straight or branched lower alkyl of from 1 to 6 carbon atoms, and straight or branched lower alkoxy of from 1 to 6 carbon atoms.

4. A compound selected from the formula:

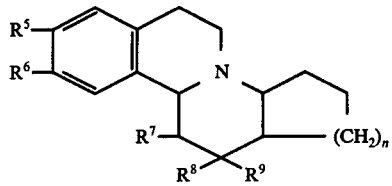

wherein each of $R^5$ and $R^6$ is selected from hydrogen, chlorine, fluorine, bromine, iodine, hydroxy, straight or branched lower alkoxy of from 1 to 4 carbon atoms, straight or branched lower alkyl of from 1 to 4 carbon atoms, trifluoromethyl,

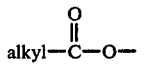

wherein the alkyl moiety has from 1 to 4 carbon atoms and may be straight or branched, alkoxycarbonyloxy, carbamoyloxy, benzoyloxy, and benzoyloxy mono-, di- or tri- substituted with straight or branched lower alkyl of from 1 to 4 carbon atoms, straight or branched lower alkoxy of from 1 to 4 carbon atoms, chlorine, fluorine, bromine, or iodine with the proviso that when one of $R^5$ or $R^6$ is trifluoromethyl, the other of $R^5$ or $R^6$ is other than trifluoromethyl; $R^7$ is selected from hydrogen, straight or branched lower alkyl of from 1 to 4 carbon atoms, phenyl and benzyl; $R^8$ is selected from hydrogen, straight or branched lower alkyl of from 1 to 4 carbon atoms, phenyl, benzyl, 2-phenethyl, mono-, di- or tri- substituted phenyl, mono-, di- or tri- substituted benzyl, mono-, di- or tri- substituted 2phenethyl wherein the substituents are on any position of the aromatic ring of each of phenyl, benzyl and 2-phenethyl and each substituent is selected from straight or branched lower alkyl of from 1 to 4 carbon atoms, straight or branched lower alkoxy of from 1 to 4 carbon atoms, chlorine, fluorine, bromine and iodine; $R^9$ is selected from hydroxy, the group

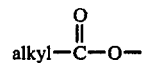

wherein the alkyl moiety has from 1 to 4 carbon atoms and may be straight or branched, alkoxycarbonyloxy, carbamoyloxy, benzoyloxy, and benzoyloxy mono-, di- or tri- substituted with straight or branched lower alkyl of from 1 to 4 carbon atoms, straight or branched lower alkoxy of from 1 to 4 carbon atoms, chlorine, fluorine, bromine, or iodine; n is an integer of from 1 to 3; and pharmaceutically acceptable acid addition salts thereof.

5. A compound of claim 4 wherein $R^7$ is selected from hydrogen, a straight chain alkyl of from 1 to 4 carbon atoms, phenyl and benzyl.

6. A compound of claim 4 wherein each of $R^5$ and $R^6$ is selected from hydrogen, chlorine, fluorine, bromine, iodine, hydroxy, straight or branched lower alkoxy of from 1 to 4 carbon atoms, a straight chain lower alkyl of from 1 to 4 carbon atoms, trifluoromethyl,

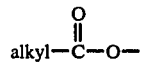

wherein the alkyl moiety has from 1 to 4 carbon atoms and may be straight of branched, alkoxycarbonyloxy, carbamoyloxy, benzoyloxy, and benzoyloxy substituted with straight or branched lower alkyl of from 1 to 4 carbon atoms, straight of branched lower alkoxy of from 1 to 4 carbon atoms, chlorine, fluorine, bromine, and iodine with the proviso that when one of $R^5$ or $R^6$ is trifluoromethyl, the other of $R^5$ or $R^6$ is other than trifluoromethyl.

7. A compound of claim 4 wherein each of $R^5$ and $R^6$ is selected from hydrogen, chlorine, fluorine, bromine, iodine, hydroxy, straight or branched lower alkoxy of from 1 to 4 carbon atoms, straight or branched lower alkyl of from 1 to 4 carbon atoms, and trifluoromethyl with the proviso that when one of $R^5$ or $R^6$ is trifluoromethyl the other of $R^5$ or $R^6$ is other than trifluoromethyl.

8. A compound of claim 7 wherein the lower alkyl group of from 1 to 4 carbon atoms is a straight chain.

9. A compound of claim 4 wherein $R^5$ is hydrogen, and $R^6$ is selected from hydrogen, chlorine, bromine, fluorine, iodine, hydroxy, straight or branched lower alkoxy of from 1 to 4 carbon atoms, straight or branched lower alkyl of from 1 to 4 carbon atoms, trifluoromethyl,

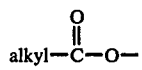

wherein the alkyl moiety has from 1 to 4 carbon atoms and may be straight or branched, alkoxycarbonyloxy, carbamoyloxy, benzoyloxy and benzoyloxy substituted with straight or branched lower alkyl to of from 1 to 4 carbon atoms, straight or branched lower alkoxy of from 1 to 4 carbon atoms, chlorine, fluorine, bromine, and iodine.

10. A compound of claim 4 wherein $R^6$ is hydrogen, and $R^5$ is selected from chlorine, fluorine, bromine, iodine, hydroxy, straight or branched lower alkoxy of from 1 to 4 carbon atoms, straight or branched lower alkyl of from 1 to 4 carbon atoms, trifluoromethyl,

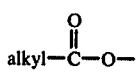

wherein the alkyl moiety has from 1 to 4 carbon atoms and may be straight or branched, alkoxy carbonyloxy, carbamoyloxy, benzoyloxy, and benzoyloxy substituted with straight or branched lower alkyl or from 1 to 4 carbon atoms, straight or branched lower alkoxy of from 1 to 4 carbon atoms, chlorine, fluorine, bromine, and iodine.

11. A compound of claim 1 which is 2,3,4,4a,6,7,11b,12,13,13a-decahydro-1H-dibenzo[a,f]quinolizin-13-ol and pharmaceutically acceptable salts thereof.

12. A compound of claim 1 which is 2,3,4,4a,6,7,11b,12,13,13a-decahydro-9,10-dimethoxy-1H-dibenzo[a,f]quinolizin-13-ol and pharmaceutically acceptable salts thereof.

13. A compound of claim 1 which is 1,2,3,3a,5,6,10b,11,12,12a-decahydrobenzo[a]cyclopenta[f]quinolizin-12-ol and pharmaceutically acceptable salts thereof.

14. A compound of claim 1 which is 2,3,4,4a,6,7,11b,12,13,13a-decahydro-13-methyl-1H-dibenzo[a,f]quinolizin-13-ol and pharmaceutically acceptable salts thereof.

15. A compound of claim 1 which is 2,3,4,4a,6,7,11b,12,13,13a-decahydro-1H-dibenzo[a,f]quinolizin-13-ol propionate ester and pharmaceutically acceptable salts thereof.

16. A compound of claim 1 which is 10-fluoro-2,3,4,4a,6,7,11b,12,13,13a-decahydro-1H-dibenzo[a,f]quinolizin-13-ol and pharmaceutically acceptable acid addition salts thereof.

17. A compound of claim 1 which is 10-methyl-2,3,4,4a,6,7,11b,12,13,13a-decahydro-1H-dibenzo[a,f]quinolizin-13-ol and pharmaceutically acceptable acid addition salts thereof.

* * * * *

UNITED STATES PATENT AND TRADEMARK OFFICE
CERTIFICATE OF CORRECTION

PATENT NO. : 4,096,147

DATED : June 20, 1978

INVENTOR(S) : Charles Andrew Lundberg

It is certified that error appears in the above-identified patent and that said Letters Patent are hereby corrected as shown below:

Column 4, line 15 "...4 carbon carbon atoms..." should read "4 carbon atoms". Column 9, Item 11, line 2 "...dodeoahydro..." should read "dodecahydro". Column 10, Item 14, line 2 "...cyclopentata..." should read "cyclopenta". Column 19, line 63 "...2phenethyl..." should read "2-phenethyl". Column 20, No. 6, line 33 "...straight of branched..." should read "straight or branched".

Signed and Sealed this

Twentieth Day of February 1979

[SEAL]

Attest:

RUTH C. MASON
Attesting Officer

DONALD W. BANNER
Commissioner of Patents and Trademarks